United States Patent [19]
Kofoed et al.

[11] Patent Number: 5,379,650
[45] Date of Patent: Jan. 10, 1995

[54] DIFFERENTIAL PRESSURE SENSOR FOR RESPIRATORY MONITORING

[75] Inventors: Scott A. Kofoed; Joseph A. Orr, both of Salt Lake City, Utah

[73] Assignee: Korr Medical Technologies Inc., Salt Lake City, Utah

[21] Appl. No.: 111,161

[22] Filed: Aug. 24, 1993

Related U.S. Application Data

[63] Continuation-in-part of Ser. No. 949,573, Sep. 23, 1992.
[51] Int. Cl.$^6$ .......................... G01F 1/46; A61B 5/087
[52] U.S. Cl. ................. 73/861.52; 73/861.75; 128/725
[58] Field of Search ........... 73/861.42, 861.52, 861.65, 73/861.66; 128/725

[56] References Cited

U.S. PATENT DOCUMENTS

| | | |
|---|---|---|
| 1,145,220 | 7/1915 | Smith . |
| 2,706,409 | 4/1955 | Preston . |
| 3,410,264 | 11/1968 | Frederick . |
| 3,449,954 | 6/1969 | Brown . |
| 3,590,473 | 7/1971 | Carlson . |
| 3,663,833 | 5/1972 | Pao et al. . |
| 3,726,271 | 4/1973 | Mondshine et al. . |
| 3,752,171 | 8/1973 | Ayre . |
| 3,910,113 | 10/1975 | Brown . |
| 4,036,054 | 7/1977 | Goulet . |
| 4,047,521 | 9/1977 | Kramer et al. . |
| 4,154,100 | 5/1979 | Harbaugh et al. ............... 73/861.66 |
| 4,170,134 | 10/1979 | Nathan . |
| 4,345,463 | 8/1982 | Wilson et al. . |
| 4,372,170 | 2/1983 | Dehart et al. . |
| 4,403,514 | 9/1983 | Osborn . |
| 4,481,829 | 11/1984 | Shortridge . |
| 4,546,655 | 10/1985 | Victor . |
| 4,581,945 | 4/1986 | Rusz . |
| 4,823,615 | 4/1989 | Taha ................. 73/861.66 |
| 4,920,808 | 5/1990 | Sommer ........... 73/861.42 |
| 5,026,255 | 6/1991 | Carpenter et al. . |
| 5,038,773 | 8/1991 | Norlien et al. . |
| 5,088,332 | 2/1992 | Merilainen et al. . |

FOREIGN PATENT DOCUMENTS

| | | |
|---|---|---|
| 699939 | 11/1953 | United Kingdom . |
| 2032118 | 4/1980 | United Kingdom ............. 73/861.66 |
| 2052074 | 1/1981 | United Kingdom . |
| 1509744 | 9/1989 | U.S.S.R. ........... 73/861.65 |

OTHER PUBLICATIONS

"Basics of Auto Referencing", Sen Sym, pp. 7–9 through 7–35, undated.

Detex brochure, "See Compliance at a Glance", undated.

Radar, Con, "Pneumotachography", The Perking Elmer Corporation, California Society of Cardiopulmonary Technologies Conference, Oct. 1982.

Saklad, Meyer, et al., "Pneumotachography: A New Low–dead space, Humidity–independent Device", *Anesthesiology*, vol. 5, No. 2, Aug. 1979, pp. 149–153.

Sullivan, William, J., et al. "Pneumotachographs: Theory and Clinical Application", *Respiratory Care*, vol. 29, No. 7, Jul. 1984, pp. 736–749.

*Primary Examiner*—Herbert Goldstein
*Attorney, Agent, or Firm*—Trask, Britt & Rossa

[57] ABSTRACT

A differential pressure sensor for measuring respiratory gas flow including a tubular housing containing a diametrically-oriented, longitudinally extending strut containing first and second lumens having longitudinally-spaced pressure ports opening into respective axially-located notches at each end of the strut.

40 Claims, 4 Drawing Sheets

DIFFERENTIAL PRESSURE SENSOR FOR RESPIRATORY MONITORING

This application is a continuation-in-part of U.S. Patent application Ser. No. 949,573, filed Sep. 23, 1992.

BACKGROUND OF THE INVENTION

1. Field of the Invention

The present invention relates to respiratory flow measurement, and specifically to improving the performance of differential pressure flowmeters under diverse inlet conditions through an improved sensor configuration.

2. State of the Art

Respiratory flow measurement during the administration of anesthesia, in intensive care environments and in monitoring the physical condition of athletes and other individuals prior to and during the course of training programs provides valuable information for assessment of pulmonary function and breathing circuit integrity. Many different technologies have been applied to create a flowmeter that meets the requirements of the critical care environment. Among the flow measurement approaches which have been employed are:

1) Differential Pressure—measuring the pressure drop or differential across a resistance to flow.
2) Spinning Vane—counting the revolutions of a vane placed in the flow path.
3) Hot Wire Anemometer—measuring the cooling of a heated wire due to airflow passing around the wire.
4) Ultrasonic Doppler—measuring the frequency shift of an ultrasonic beam as it passes through the flowing gas.
5) Vortex Shedding—counting the number of vortices that are shed as the gas flows past a strut placed in the flow stream.
6) Time of Flight—measuring the arrival time of an impulse of sound or heat created upstream to a sensor placed downstream.

Each of the foregoing approaches has various advantages and disadvantages, and an excellent discussion of most of these aforementioned devices may be found in W.J. Sullivan; G.M. Peters; P.L. Enright, M.D.; "*Pneumotachographs: Theory and Clinical Application,*"*Respiratory Care*, July 1984, Vol. 29-7, pp. 736–49, and in C. Rader, *Pneumotachography*, a report for the Perkin-Elmer Corporation presented at the California Society of Cardiopulmonary Technologists Conference, Oct. 1982.

At the present time, the most commonly employed device for respiratory flow measurement is the differential pressure flowmeter. Because the relationship between flow and the pressure drop across a restriction or other resistance to flow is dependent upon the design of the resistance, many different resistance configurations have been proposed. The goal of all of these configurations is to achieve a linear relationship between flow and pressure differential. It should be noted at this point that the terms "resistance" and "restriction" as applied herein to the physical configuration which produces a pressure drop or differential for use as a flowmeter input signal may be used interchangeably.

In some prior art differential pressure flowmeters (commonly termed pneumotachs) the flow restriction has been designed to create a linear relationship between flow and differential pressure. Such designs include the Fleisch pneumotach in which the restriction is comprised of many small tubes or a fine screen, ensuring laminar flow and a linear response to flow. Another physical configuration is a flow restriction having an orifice variable in relation to the flow. This arrangement has the effect of creating a high resistance at low flows and a low resistance at high flows. Among other disadvantages, the Fleisch pneumotach is susceptible to performance impairment from moisture and mucous, and the variable orifice flowmeter is subject to material fatigue and manufacturing variabilities.

U.S. Pat. No. 5,038,773 discloses a differential pressure flowmeter sensor which employs a plurality of pressure ports or apertures symmetrically disposed on the leading and trailing edges of hollow cruciform ribs divided to define two sets of lumens and extending across the cross-section of a tubular housing. U.S. Pat. No. 5,088,332 discloses a differential pressure flowmeter sensor having first and second pressure ports or apertures axially disposed within a tubular housing and supported therein by longitudinally-extending vanes or baffles including surfaces thereon for collecting and guiding pressure generated by gas flowing in the housing to the pressure ports. The flowmeter designs of the foregoing patents are intended to address deficiencies in other prior art flowmeter sensors with regard to performance impairment due to moisture and mucous, and to provide a simple design permitting economical manufacture and, if desired, disposability.

All of the prior art flowmeter sensors referenced above, however, are susceptible to performance impairment and inaccuracies relating to changes in gas flow inlet conditions. In many applications, such variances are avoided or compensated for by employing a flow conditioner, such as a screen or a straight tubing section to provide known flow characteristics to the gas flow entering the sensor. However, in respiratory monitoring applications, the exact geometry of the components "upstream" of the sensor ("upstream" being bi-directional, as both inspiration and expiration of the patient are monitored) may vary widely based upon the preference of the clinician and the needs of the patient. In addition, the added volume and resistance to flow resulting from the deployment of a flow conditioner diminish respiratory gas exchange, a particularly undesirable situation with anaesthetized patients.

Differential pressure flowmeters of the prior art employing pressure ports which are flush with the conduit wall, spaced therefrom or facing directly into the gas flow are susceptible to localized pressure effects, Bernoulli effects, and pitot tube effects. Pressure port design in the prior art has failed to minimize such effects and to make prior art flowmeters independent of upstream geometry without adding significant volume to the system and/or substantial resistance to flow.

Localized pressure effects arise in flowmeters when gas flow inlet conditions are asymmetrical, such as occurs when a bend is placed in the flow path in close proximity to the sensor, when a jet or nozzle intrudes on the flow stream, or when any non-symmetrical obstruction is placed in the inlet-stream.

The Bernoulli effect occurs when fluid flow passes over a tube or other structure placed perpendicular to the direction of flow, the flow over the obstruction causing a vacuum which leads to errors in the measurement of differential pressure across an obstruction to the flow.

The pitot tube effect, or "ram" effect, is related to flow velocity, as the port of a pitot tube faces toward the direction of gas flow. When a nozzle or jet is placed upstream of a sensor, a localized high velocity flow is created in the center of the flow stream, leading to erroneous results in devices of the type disclosed in the prior art.

The flow sensor design of the aforementioned '773 patent is susceptible to error from all of the above phenomena, by virtue of the use of a large number of small pressure ports or apertures placed about the cross-section of the housing bore and the placement of such ports facing the flow direction on the leading edges of the supporting ribs. The '773 sensor is also susceptible to clogging and error from mucous and other patient fluids due to the close proximity of some of the ports to the inner wall of the sensor housing.

The flow sensor design of the aforementioned '332 patent is somewhat less susceptible to clogging from patient fluids due to its axial port location, but is very susceptible to localized pressure effects due to the configuration of the leading faces of the vanes or baffles supporting the pressure ports, which structure collects or focuses the gas flow from across the cross section of the sensor housing bore directly into the pressure ports. This configuration also renders the device of the '332 patent very susceptible to error from the pitot tube effect under certain inlet conditions, and has been demonstrated to unduly limit the dynamic range of the device.

In short, all known prior art differential pressure flow sensors suffer deficiencies when exposed to less than ideal gas flow inlet conditions, and further possess inherent design problems with respect to their ability to sense differential pressure in a meaningful, accurate, repeatable manner over a substantial dynamic flow range.

SUMMARY OF THE INVENTION

The present invention comprises a differential pressure sensor for a differential pressure flowmeter for respiratory monitoring, the sensor of the invention having the capability of accommodating a wide variety of gas flow inlet conditions while employing a minimum of added system volume or resistance to flow. The design of the sensor of the present invention also substantially prevents the entrance of liquids in the monitoring system into the pressure ports of the sensor.

The sensor of the present invention comprises a substantially tubular housing having disposed in the bore thereof a diametrically-oriented, longitudinally-extending strut having pressure ports located adjacent each end of the strut. The pressure ports are each associated with a lumen contained within the strut, the lumens extending to the exterior of the sensor for communication via suitable tubing with a differential pressure transducer. Depending upon whether inspiration or expiration differential pressure is being measured, one port serves as a high pressure tap and the other as a low pressure tap.

In the preferred embodiment, the pressure ports are oriented substantially perpendicular to the axis of the tubular housing, and communicate with the interior volume of the housing via axially-placed notches in the leading and trailing edges of the strut. It is preferred that the notches extend over the entire width of the strut in the area of the pressure ports and through the side faces of the strut so that the pressure ports have reduced response to the velocity of mass flow through the sensor.

DETAILED DESCRIPTION OF THE PREFERRED EMBODIMENTS

Figure 1:
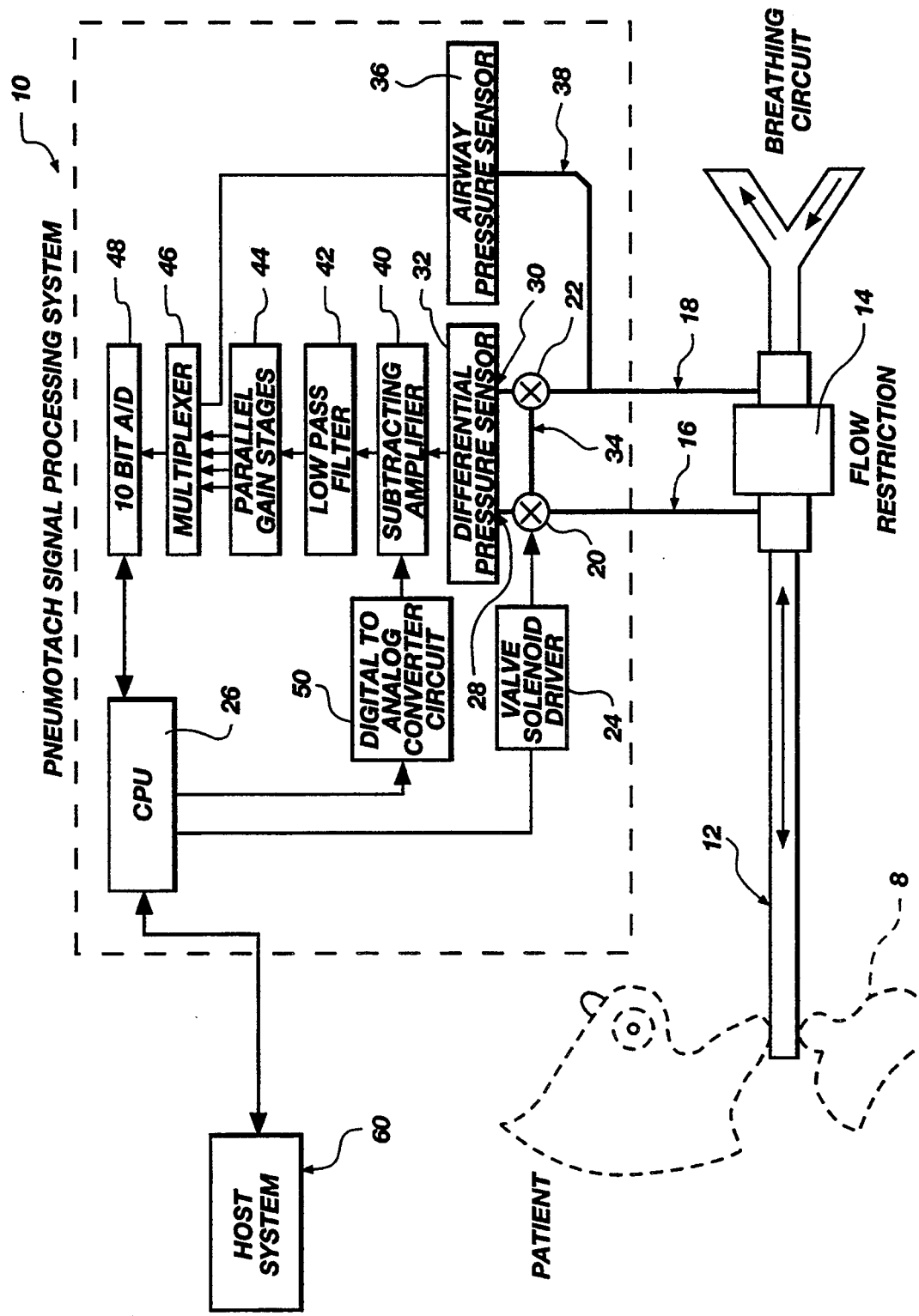
FIG. 1 is a schematic of an apparatus for respiratory flow measurement including a flow sensor according to the present invention, in combination with a differential pressure transducer and signal processing system.

FIG. 1 of the drawings schematically depicts a differential pressure flowmeter 10, with a patient 8 breathing through a respiration tube 12 having a differential pressure sensor 14 according to the present invention employed therewith, the pressures detected by sensor 14 being converted by a differential pressure transducer to an electrical signal which is then processed as hereinafter described.

First and second pressure takeoff tubes 16 and 18, one in communication with the interior of sensor 14 on each side of a flow restriction incorporated therein, extend respectively to first and second three-way valves 20 and 22 driven by solenoid driver 24 in response to commands from central processing unit (CPU) 26. Valves 20 and 22 are configured to provide communication in a first mode or position from breathing tube 12 through first and second takeoff tubes 16 and 18 to pressure ports 28 and 30 of differential pressure transducer 32, and in a second mode or position between ports 28 and 30 through shunt or bypass tube 34 in isolation from respiration tube 12 for auto-referencing.

Airway pressure sensor 36 is in communication with respiration tube 12 through auxiliary pressure takeoff tube 38 which connects to second pressure takeoff tube 18 between valve 22 and respiration tube 12. Differential pressure transducer 32 provides an analog signal to subtracting amplifier 40, which in turn provides a signal to a plurality of amplifiers providing different parallel gain stages 44 through low pass filter 42. The signals from each of the gain stages 44, in conjunction with a signal from airway pressure sensor 36, are received by multiplexer 46 and forwarded to ten bit analog-to-digital converter 48 under control of CPU 26. Digital-to-analog converter circuit 50 is also included in the signal processing system employed in differential pressure flowmeter 10. CPU 26 communicates the signal processing system with a host system 60 such as a personal computer with readout, display and/or alarm means associated therewith.

A preferred embodiment of a gas flow and circuit schematic for flowmeter 10 with parallel gain realization as described above is depicted and described in the previously-referenced U.S. Patent application Ser. No. 949,573, filed Sep. 23, 1992, assigned to the assignee of the present invention, and incorporated herein for all purposes by this reference. The '573 application also depicts and describes an alternative embodiment of a gas flow and circuit schematic for flowmeter 10 with series gain realization. However, such circuits and their operation form no part of the differential pressure sensor of the present invention as hereinafter claimed, and therefore no further description thereof will be made in this application.

Referring now to FIGS. 2 through 5 of the drawings, a preferred embodiment 100 of the differential pressure sensor 14 of the present invention is depicted. Preferred sensor embodiment 100 is preferably a unitary, injection-molded plastic element, so as to afford low manufacturing cost and permit disposal of the sensor after a single use, although this is not a requirement and the materials and method of fabrication are not critical to the invention. Suitable plastics include polycarbonates such as Lexan ®, manufactured by General Electric or Makroion ®, manufactured by Miles Chemicals.

Preferred sensor embodiment 100 includes a tubular housing 102 having a bore of substantially circular cross-section, within which diametrically-oriented longitudinally-extending strut 104 of axial length L and height H1 is disposed. Strut 104, which provides resistance to respiratory gas flow in tubular housing 102, is secured at both ends to the inner wall 106 of housing 102, has first and second end faces 108 and 110 and first and second side faces 112 and 114. The cross-sectional area of strut 104 should be at least equal to ten percent (10%) of the cross-sectional bore area of the sensor housing 102 at the strut location to provide sufficient restriction to gas flow for effective operation of sensor 100.

Figure 2:
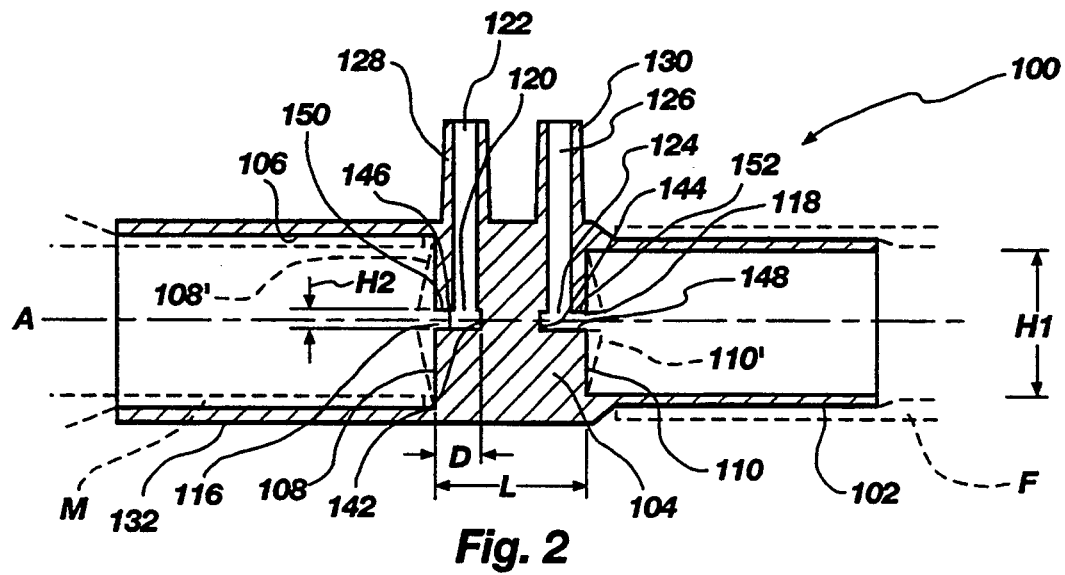
FIG. 2 is a side sectional elevation of a preferred embodiment of the differential flow sensor of the present invention.
Figure 3:
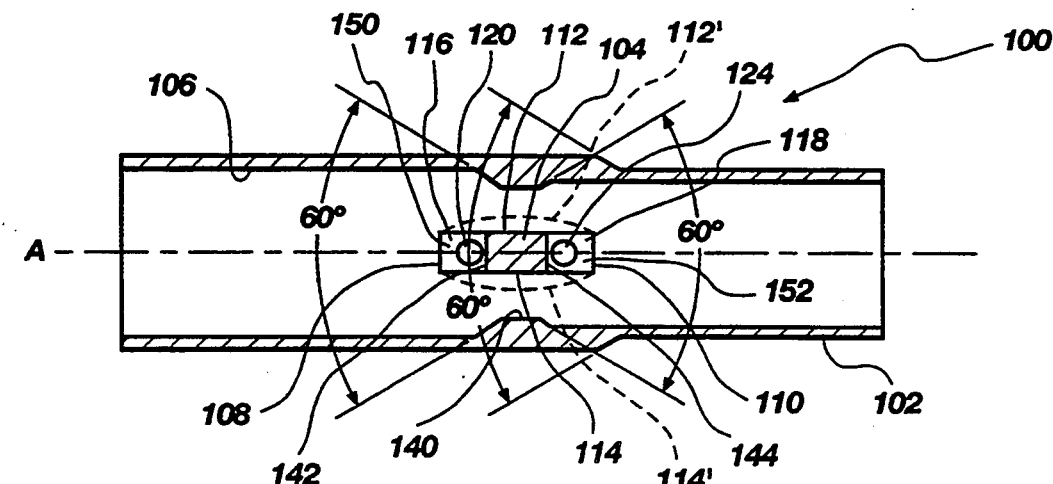
FIG. 3 is a sectional elevation of the sensor configuration of FIG. 2, looking upward from a plane extending laterally across the axis of the sensor.
Figure 4:
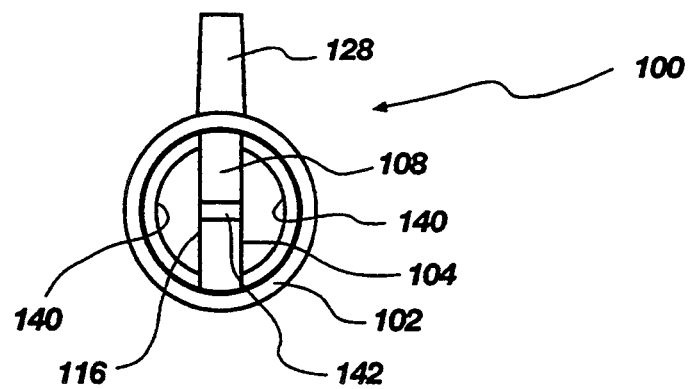
FIG. 4 is an end view of the sensor configuration of FIG. 2.
Figure 5:
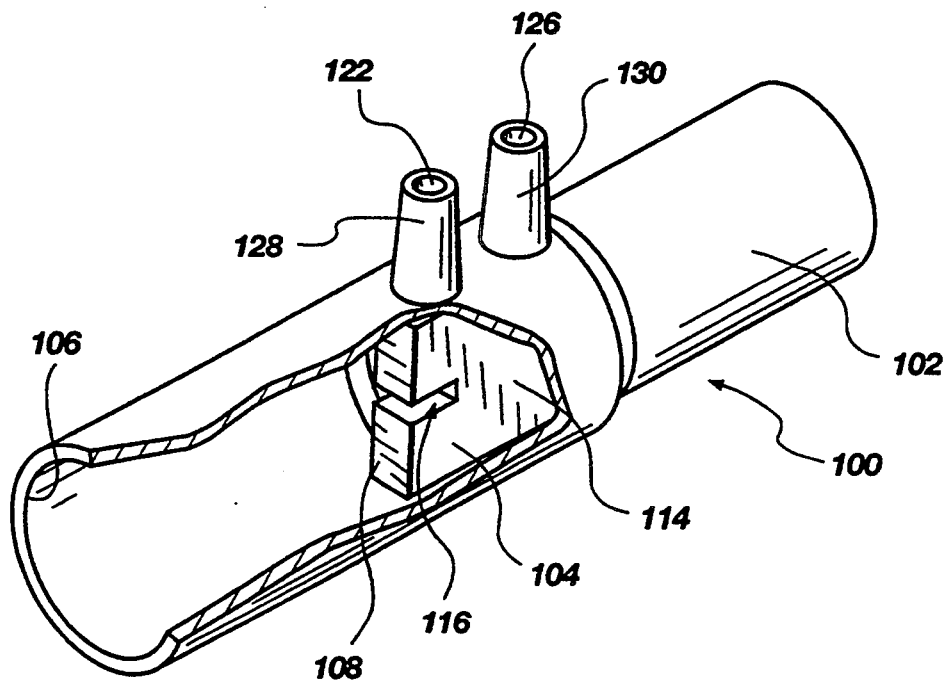
FIG. 5 is a perspective, partial cutaway isometric view of the sensor configuration of FIG. 2.
Figure 6A:
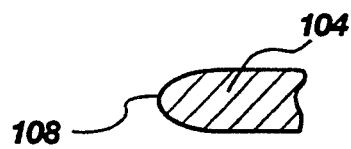
FIGS. 6A through 6D depict alternative cross-sectional configurations for the end faces and notch back walls of the sensor configuration of FIG. 2.
Figure 6B:
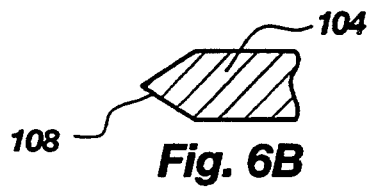
Figure 6C:
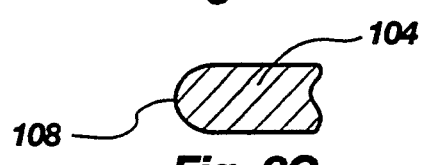
Figure 6D:
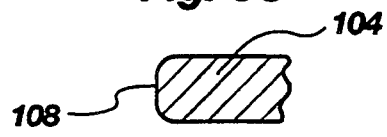

It should be noted that the bore diameter of the tubular housing 102 depicted in FIGS. 2 and 3 is different on both ends of strut 104. This is intentional in the preferred embodiment, to accommodate a male connecting tube element shown in broken lines and designated as M on the left-hand side of the sensor, and a female connecting tube element F on the right-hand side of the sensor. Thus, in use, the effective inner diameter of housing 102 remains substantially constant, although this is not a requirement of the invention and in some instances sensor 100 may be modified to have differing effective diameters on each side of strut 104 so as to accommodate different dynamic flow ranges during patient inspiration and expiration.

Strut 104 further includes notch means comprising substantially symmetrical notches 116 and 118 located substantially on axis A of housing 102, notches 116 and 118 extending axially inwardly from first and second end faces 108 and 110, respectively, and laterally through first and second sides faces 112 and 114. Pressure port 120 of lumen 122 opens into notch 116, and pressure port 124 of lumen 126 opens into notch 118, lumens 122 and 126 comprising passages internal to strut 104 which extend into and through male luers or nipples 128 and 130 on the exterior surface 132 of tubular housing 102.

Both pressure ports 120 and 124 face substantially perpendicular to axis A of housing 102, notches 116 and 118 extend axially inwardly to a depth D at least past pressure ports 120 and 124, and may so extend a distance equal to the height H2 of the notches 116 and 118, which in turn should be less than or equal to four-tenths (4/10) of the height H1 of the strut 104.

As previously noted, resistance to gas flow in embodiment 100 of sensor 14 is created at least by the presence of strut 104 in housing 102, and the width and length of strut 104 may be altered as desired to change flow characteristics. Further resistance to flow may be created by reducing the cross-sectional bore area open to flow though housing 102 adjacent the inner wall 106 of tubular housing 102 in the vicinity of the strut 104, either by necking down the inner wall 106 to a smaller diameter as shown at 140 in FIG. 2, or by placing material on the inner wall 106 in a symmetrical pattern. It is desirable, when necking down the inner diameter of housing 102 as shown at 140, to make a gradual transition in diameter with chamfered surfaces as shown in FIG. 2 to minimize disruption in the gas flow and also to prevent patient fluids from collecting in the sensor housing 102. While 60° chamfers have been illustrated by way of example, other angles and non-linear transition surfaces may also be employed. It has been found that decreasing the cross-sectional area of housing 102 adjacent inner wall 106 in the vicinity of strut 104 may be effected without impairing the performance characteristics of sensor 14 if the constricted or reduced cross-sectional area does not extend an axial distance beyond each strut end face 108 and 110 greater than about twenty-five percent (25%) of the length L of strut 104.

It is contemplated that end faces 108 and 110 may be flat and substantially perpendicular to axis A as shown in FIG. 2, or may be rounded, beveled, chamfered or otherwise shaped as shown in FIGS. 6A through 6D, so long as the end face configuration is symmetrical when viewed from above, as in FIG. 3. Furthermore, end faces 108 and 110 may actually incline outwardly toward axis A, so that notches 116 and 118 commence at axially-protruding locations on strut 104, as shown in broken lines referenced as 108' and 110' in FIG. 2. Finally, end faces 108 and 110 may be of arcuate or other nonlinear configuration when viewed from the side as in FIG. 2. The major characteristic of end faces 108 and 110, aside from symmetry, is that they do not incline toward notches 116 and 118 or otherwise collect or direct flow though sensor 100 toward the notches and pressure ports.

Side faces 112 and 114 of strut 104 may be flat as shown in FIG. 2, or may be of convex or other curvilinear configuration as shown in broken lines referenced as 112' and 114', again the major requirement as with end faces 108 and 110 being one of symmetry between the sides of strut 104.

The back walls 142 and 144 of notches 116 and 118 may be flat as shown in FIG. 3, or be radiused, beveled, chamfered or otherwise symmetrically shaped, as with the end faces 108 and 110, the end face configurations illustrated in FIGS. 6A through 6D being equally applicable to back walls 142 and 144.

The floors 146 and 148 and ceilings 150 and 152 may be flat as shown in FIG. 2, or may be rounded or otherwise symmetrically shaped. Likewise, the transition edges or lines between the end faces 108 and 110 and the notches 116 and 118 may be abrupt or sharp as illustrated, or radiused, chamfered, bevelled or otherwise modified.

The foregoing modifications of the sensor embodiment of FIGS. 2 through 5 may be selectively employed to adapt to the conditions under which sensor is to operate. In particular, the modification of the cross-sectional flow area in the vicinity of strut 104 may be employed to adjust the dynamic range of sensor 100, as may modifications to the configuration of the end faces, the back walls of the notches, and to the lines of transition between the notches and the end faces and side faces. The use of both center (strut) restrictions and inner wall restrictions to flow adds symmetry to the flow pattern, normalizes the flow and provides better repeatability of readings. The notch height H2 may be increased to accommodate a wider range of inlet conditions, such as might result from employment of sensor 100 with a variety of endotracheal tubes, a high notch providing an averaging effect.

Figure 7:
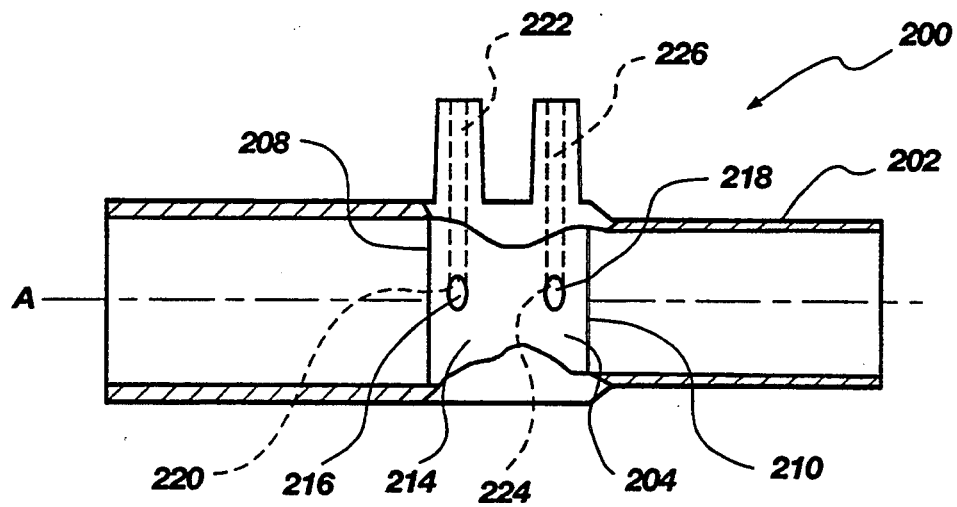
FIG. 7 is a side partial-sectional elevation of an alternative embodiment of the differential pressure sensor of the present invention.
Figure 8:
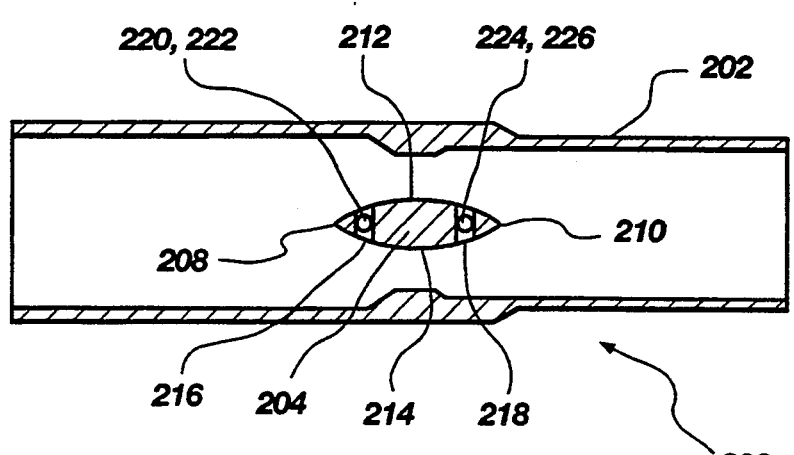
FIG. 8 is a sectional elevation of the sensor configuration of FIG. 7, looking upwardly from a plane extending laterally across the axis of the sensor.

FIGS. 7 and 8 depict an alternative embodiment 200 of the differential pressure sensor of the present invention, sensor 200 including an aerodynamically-shaped or streamlined strut 204 with tapered edges 208 and 210 rather than end faces. In lieu of notches axially or longitudinally opening into the gas flow stream, sensor 200 includes chambers 216 and 218 extending through the width of struts 204 and having pressure ports 220 and 224 opening thereinto, ports 220 and 224 communicating with the exterior of sensor 200 via lumens 222 and 226, respectively. If desired, chambers 216 and 218 may not extend through strut 204, but may comprise recesses in the side faces 212 and 214 which communicate with lumens 222 and 226 via a manifold having ports opening into both recesses. Sensor configuration 200 is more aerodynamic than sensor 100, is less sensitive to the pitot tube effect, and thus may be more suitable for measurement at higher flow rates and over a greater dynamic range.

While the differential pressure sensor of the present invention has been disclosed herein in terms of a preferred and alternative embodiment and modifications thereto, those of ordinary skill in the art will appreciate that many other additions, deletions and modifications to the disclosed embodiments may be effected without departing from the scope of the invention as hereinafter claimed.

What is claimed is:

1. A differential pressure sensor for measuring respiratory gas flow, said differential pressure sensor comprising:
    a tubular housing having a bore and a longitudinal axis; a strut diametrically disposed and longitudinally extending within said tubular housing bore, said strut having a first end face, a second end face, a first side face, a second side face, and an axial length along the longitudinal axis of said tubular housing;
    first and second longitudinally spaced notch means in said strut located proximate said longitudinal axis of said tubular housing for allowing said respiratory gas flow thereinto, said first notch means extending from said first end face axially inward into said strut and from said first side face to said second side face, said second notch means extending from said second end face axially inward into said strut and from said first side face to said second side face; and
    first and second pressure ports respectively opening into said first and second notch means from first and second lumens contained within said strut and extending to the exterior of said tubular housing.

2. The differential pressure sensor of claim 1, wherein said first and second pressure ports face substantially perpendicular to said longitudinal axis of said tubular housing.

3. The differential pressure sensor of claim 2, wherein said first and second notches extend longitudinally into said strut at least as far as the longitudinally innermost extents of said first and second pressure ports.

4. The differential pressure sensor of claim 1, wherein said notch means have a height perpendicular to said longitudinal axis of said tubular housing less than or equal to about four-tenths of the height of said strut, taken in the same direction.

5. The differential pressure sensor of claim 1, wherein said strut has a cross-sectional area of at least about ten percent of that of the bore of said tubular housing at the location of said strut.

6. The differential pressure sensor of claim 1, wherein said bore of said tubular housing is constricted adjacent the bore wall proximate the location of said strut.

7. The differential pressure sensor of claim 6, wherein said constriction of said bore comprises a reduction in bore diameter.

8. The differential pressure sensor of claim 6, wherein said constriction comprises material affixed to said bore wall.

9. The differential pressure sensor of claim 6, wherein said constriction is located within said bore in an area, the longitudinal extent of which reaches beyond said strut no more than substantially twenty-five percent of the length of said strut.

10. The differential pressure sensor of claim 1, wherein said tubular housing bore proximate one longitudinal extent of said strut is greater in diameter than said tubular housing bore proximate the other longitudinal extent of said strut.

11. The differential pressure sensor of claim 1, wherein said strut has first and second tapered longitudinal edges.

12. The differential pressure sensor of claim 1, wherein said first and second end faces are oriented perpendicular to said longitudinal axis.

13. The differential pressure sensor of claim 1, wherein said strut includes first and second longitudinal end faces inclined away from said strut and toward said notch means wherein said axial length of said strut is greater proximate said notch means than said axial length of said strut proximate said tubular housing.

14. The differential pressure sensor of claim 1, wherein said strut is aerodynamically-shaped.

15. The differential pressure sensor of claim 1, wherein said strut includes material affixed thereto to restrict said respiratory gas flow through said tubular housing.

16. A differential pressure sensor for measuring respiratory gas flow, said differential pressure sensor comprising:
    a tubular housing having a bore and a longitudinal axis, said bore having a first portion and a second portion, the diameter of said first portion being greater than the diameter of said second portion;
    a strut diametrically disposed and longitudinally extending within said tubular housing bore, said strut having a first end face proximate said first portion of said bore of said tubular housing and having a second end face proximate said second portion of said bore of said tubular housing;

first and second longitudinally spaced notch means in said strut located proximate said longitudinal axis of said tubular housing for allowing said respiratory gas flow thereinto; and first and second pressure ports respectively opening into said first and second notch means from first and second lumens contained within said strut and extending to the exterior of said tubular housing.

17. The differential pressure sensor of claim 16, wherein said first and second notch means comprise first and second notches respectively opening into said first end face and said second end face.

18. The differential pressure sensor of claim 16, wherein said strut includes first and second side faces, and said first and second notch means each open into both said first and said second side faces of said strut.

19. The differential pressure sensor of claim 16, wherein said first and second pressure ports face substantially perpendicular to said longitudinal axis of said tubular housing.

20. The differential pressure sensor of claim 19, wherein said first and second notches extend longitudinally into said strut at least as far as the longitudinally innermost extents of said first and second pressure ports.

21. The differential pressure sensor of claim 16, wherein said notch means have a height perpendicular to said longitudinal axis of said tubular housing less than or equal to about four-tenths of the height of said strut, taken in the same direction.

22. The differential pressure sensor of claim 16, wherein said strut has a cross-sectional area of at least about ten percent of that of the bore of said tubular housing at the location of said strut.

23. The differential pressure sensor of claim 16, wherein said bore of said tubular housing is constricted adjacent the bore wall proximate the location of said strut.

24. The differential pressure sensor of claim 23, wherein said constriction comprises material affixed to said bore wall.

25. The differential pressure sensor of claim 16, wherein said first and second notch means comprise first and second notches opening into said first and second strut end faces, and said first and second notches each extend longitudinally into said strut a distance no greater than the respective height of that notch.

26. The differential pressure sensor of claim 16, wherein said strut includes side faces and said first and second notch means comprise apertures in said side faces and spaced from said first and second end faces of said strut.

27. The differential pressure sensor of claim 26, wherein said apertures comprise open chambers extending transversely through said strut.

28. The differential pressure sensor of claim 16, wherein said strut includes material affixed thereto to restrict said respiratory gas flow through said tubular housing.

29. A differential pressure sensor for measuring respiratory gas flow, said differential pressure sensor comprising:

tubular housing means for said flow of said respiratory gas therethrough, said tubular housing means having a bore having, in turn, a diameter and a longitudinal axis;

strut means for providing resistance to said flow of said respiratory gas, said strut being diametrically disposed and longitudinally extending within said tubular housing bore;

first and second longitudinally spaced notch means in said strut for allowing said respiratory gas flow thereinto, said first and second longitudinally spaced notch means each having a first wall portion for providing an area for measuring the pressure of said respiratory gas flow and a second back wall portion for said respiratory gas flow therearound from said notch means through said tubular housing; and first and second pressure port means for allowing said flow of respiratory gas thereinto, said first and second pressure port means respectively opening into said first wall portion of each of said first and second notch means from first and second lumens contained within said strut means and extending to the exterior of said tubular housing wherein each of said first and second pressure port means being located in said first wall portion a distance away from said second back wall portion of said notch means.

30. The differential pressure sensor of claim 29, wherein said strut includes first and second end faces and said first and second notch means comprise first and second notches respectively opening into said first and second end faces of said strut.

31. The differential pressure sensor of claim 29, wherein said strut includes first and second side faces, and said first and second notch means each open into both said first and said second side faces of said strut.

32. The differential pressure sensor of claim 29, wherein said first and second pressure ports face substantially perpendicular to said longitudinal axis of said tubular housing.

33. The differential pressure sensor of claim 29, wherein said strut includes first and second end faces, said first and second notch means comprise first and second notches respectively opening into said first and second end faces of said strut, and said first and second notches extend longitudinally into said strut at least as far as the longitudinally innermost extents of said first and second pressure ports.

34. The differential pressure sensor of claim 33, wherein said bore of said tubular housing is constricted adjacent the bore wall proximate the location of said strut.

35. The differential pressure sensor of claim 29, wherein said constriction of said bore comprises a reduction in bore diameter.

36. The differential pressure sensor of claim 35, wherein said constriction comprises material affixed to said bore wall.

37. The differential pressure sensor of claim 29, wherein said tubular housing bore proximate one longitudinal extent of said strut is greater in diameter than said tubular housing bore proximate the other longitudinal extent of said strut.

38. The differential pressure sensor of claim 29, wherein said strut includes first and second end faces, said first and second notch means comprise first and second notches opening into said first and second end faces of said strut, and said first and second notches each extend longitudinally into said strut a distance no greater than the respective height of that notch.

39. The differential pressure sensor of claim 29, wherein said strut is aerodynamically shaped.

40. The differential pressure sensor of claim 29, wherein said strut means includes material affixed thereto to restrict said respiratory gas flow through said tubular housing.

* * * * *

UNITED STATES PATENT AND TRADEMARK OFFICE
CERTIFICATE OF CORRECTION

PATENT NO. : 5,379,650
DATED : January 10, 1995
INVENTOR(S) : Kofoed et al.

It is certified that error appears in the above-indentified patent and that said Letters Patent is hereby corrected as shown below:

Title Page:

Item 56, Other Publications (2nd document), change "Detex" to --Datex--;

Column 5, line 27, change "Makroion" to --Makrolon--;

In Column 10, line 41, change "claim 33" to --claim 29--.

Signed and Sealed this

Ninth Day of May, 1995

Attest:

BRUCE LEHMAN

Attesting Officer

Commissioner of Patents and Trademarks